United States Patent [19]

Tenold

[11] Patent Number: 5,250,663
[45] Date of Patent: Oct. 5, 1993

[54] PREPARING ESSENTIALLY MONOMERIC NORMAL HUMAN SERUM ALBUMIN

[75] Inventor: Robert A. Tenold, Suisun City, Calif.

[73] Assignee: Miles Inc., Berkeley, Calif.

[21] Appl. No.: 848,439

[22] Filed: Mar. 9, 1992

Related U.S. Application Data

[62] Division of Ser. No. 511,362, Apr. 19, 1990.

[51] Int. Cl.⁵ .......................... C07K 3/24; C07K 15/06
[52] U.S. Cl. ..................... 530/364; 530/362; 530/363
[58] Field of Search ............... 530/364, 363, 362, 419, 530/424; 514/12

[56] References Cited

U.S. PATENT DOCUMENTS

| | | | |
|---|---|---|---|
| 2,705,230 | 3/1955 | Reid | 530/364 X |
| 2,765,299 | 10/1956 | Porsche et al. | 530/364 |
| 3,926,939 | 12/1975 | Ivano et al. | 530/364 |
| 3,992,367 | 11/1976 | Plan et al. | 530/364 |
| 4,025,500 | 5/1977 | Garcia et al. | 530/364 X |
| 4,156,681 | 5/1979 | Schneider et al. | 530/364 |
| 4,164,496 | 8/1979 | Hao | 530/364 |
| 4,222,934 | 9/1980 | Hao | 530/364 |
| 4,228,154 | 10/1980 | Fisher et al. | 530/364 |
| 4,754,019 | 6/1988 | Gion et al. | 530/364 |
| 4,764,279 | 8/1988 | Tayot et al. | 530/364 |

FOREIGN PATENT DOCUMENTS

| | | |
|---|---|---|
| 0141025 | 4/1980 | Fed. Rep. of Germany . |
| 0221180 | 4/1985 | Fed. Rep. of Germany . |
| 0467536 | 6/1976 | U.S.S.R. . |
| 0712089 | 1/1980 | U.S.S.R. . |

OTHER PUBLICATIONS

Schneider et al., "An Alternative Method of Large Scale Plasma Fractionation . . . ", Blut, vol. 30, pp. 121-134 (1975).

Primary Examiner—Michael G. Wityshyn
Assistant Examiner—C. Sayala
Attorney, Agent, or Firm—James A. Giblin; Elizabeth F. Enayati

[57] ABSTRACT

A composition is disclosed which comprises a solution of human serum albumin essentially free of chemicals used in processing. The preparation is also essentially free of metals such as aluminum. The composition is 100% pure by cellulose acetate electrophoresis and is essentially monomeric when tested by high pressure liquid chromatography. The turbidity is less than 5 N.T.U. (National Turbidity Units). This preparation has a substantially longer shelf life and remains biologically active longer than products currently available. The novelty of this product is also such that it does not leach metallic substances such as aluminum from its closure. Novel applications of process methodology are taught in the preparation of this composition and a novel preparation results from essentially non hemoglobin containing albumin sources such as Source Plasma (Human).

2 Claims, 5 Drawing Sheets

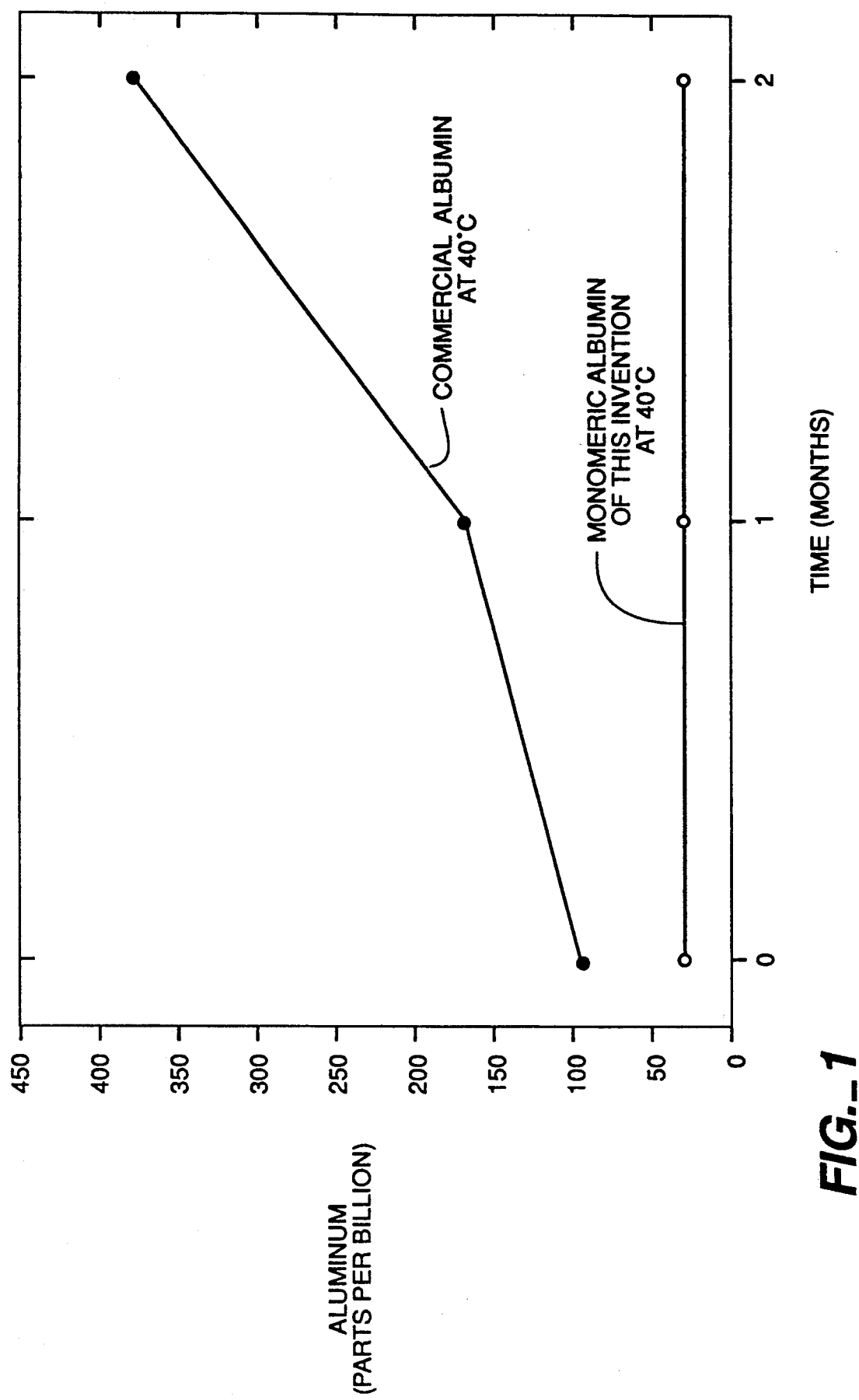
FIG._1

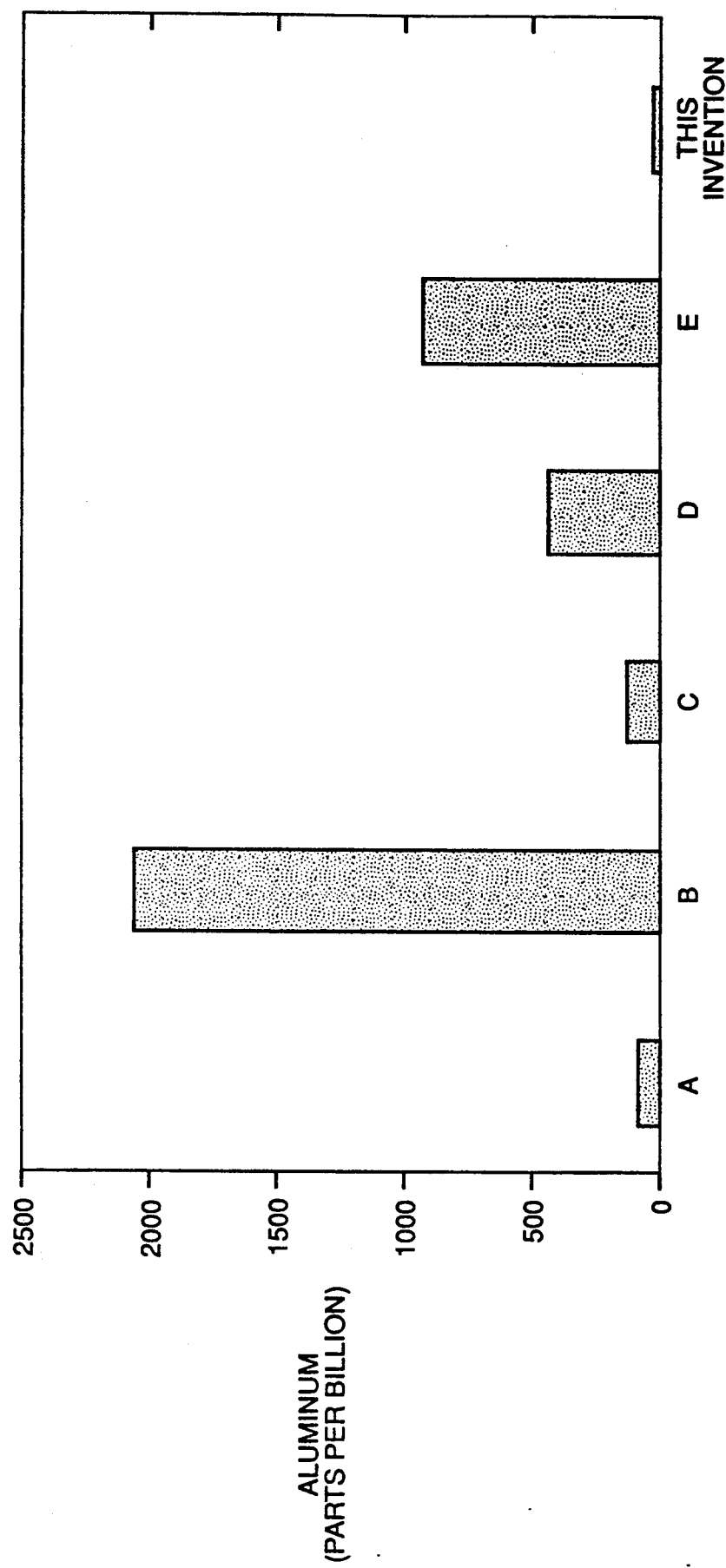
FIG._2

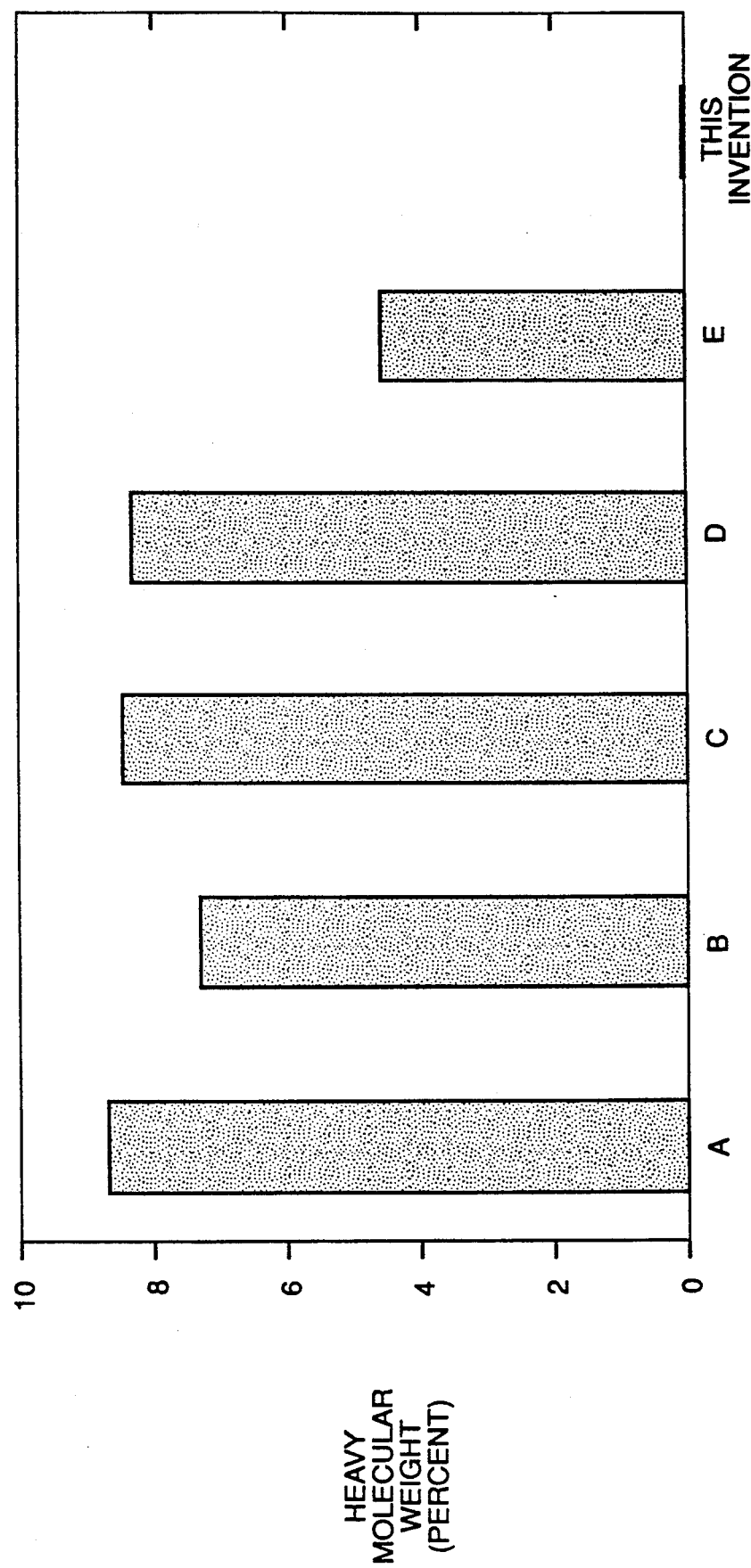
FIG._3

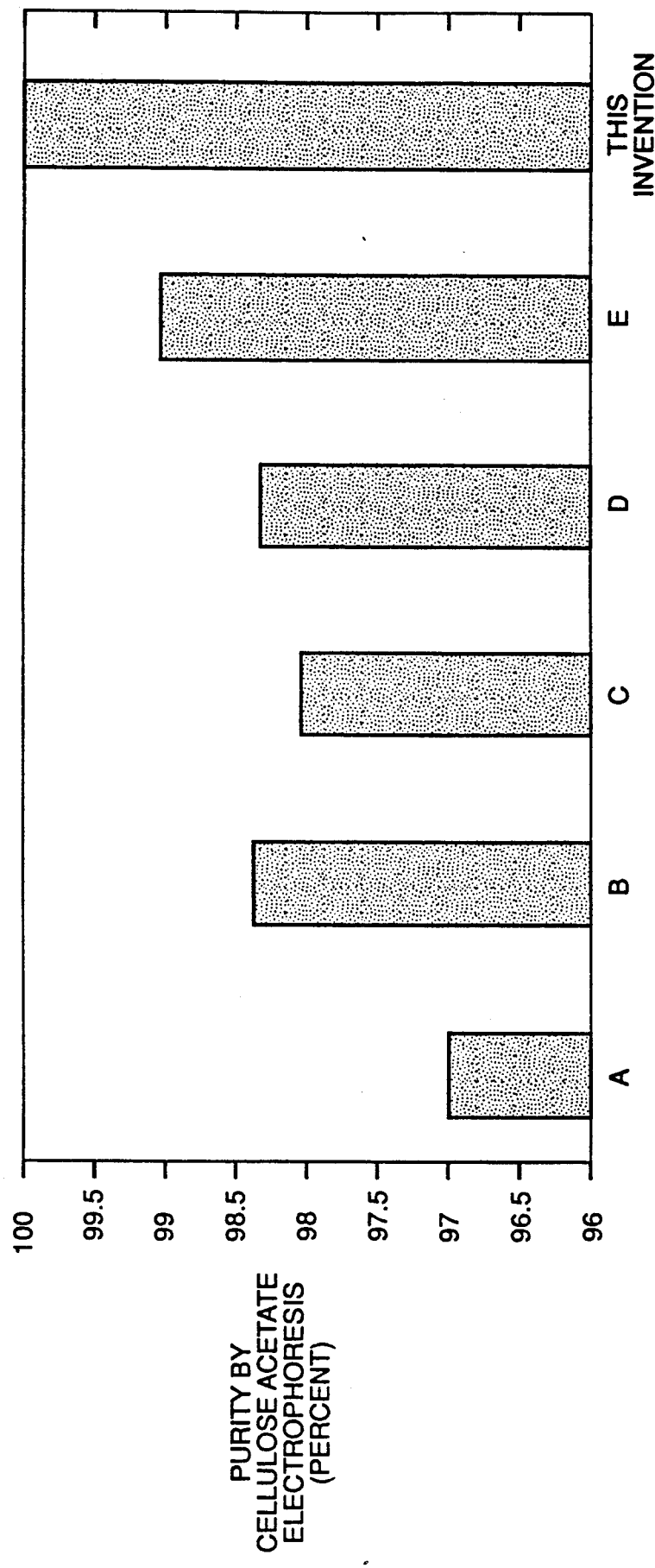
FIG._4

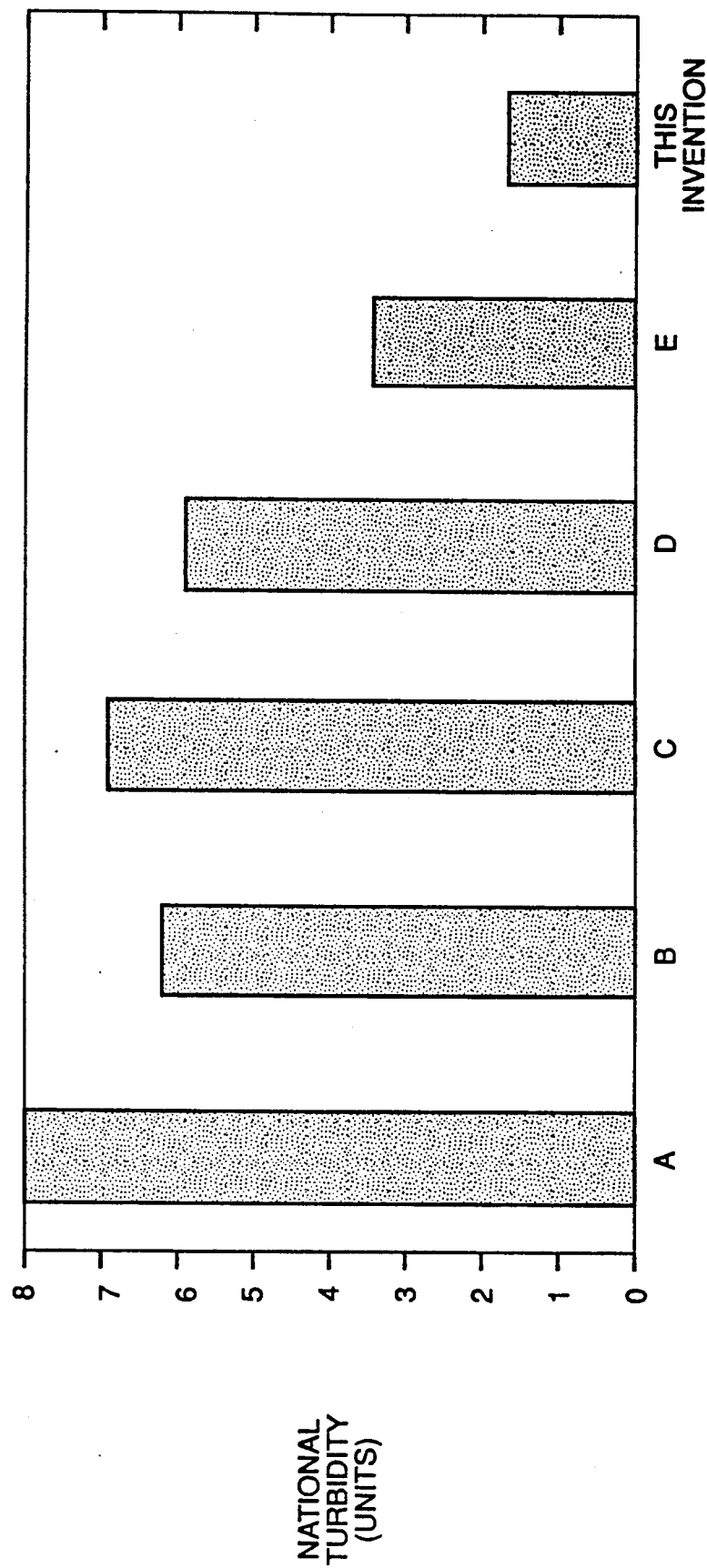
FIG._5

PREPARING ESSENTIALLY MONOMERIC NORMAL HUMAN SERUM ALBUMIN

This application is a division of application Ser. No. 07/511,362, filed Apr. 19, 1990.

FIELD OF THE INVENTION

This invention relates to therapeutic compositions comprising novel formulations and processes to obtain a purer and safer preparation of Normal Serum Albumin (Human) essentially free of aluminum and other intoxicants. Certain formulations herein described permit substantially extended dating periods for at least the following three reasons: 1) absence of heavy molecular weight components, 2) the removal of aluminum and other contaminants, and 3) the purity (100%). Labeled levels remain constant throughout the dating period.

The use of human albumin as a therapeutic is well known. One such product is "PLASBUMIN" 25% and 5% (Cutter Biological, Miles Inc., Berkeley, Calif.). Many have sought to improve albumin preparations, and it has been shown that some have achieved some level of improved composition. But each in some manner lacks attributes of this novel composition. For example: One manufacturer of albumin reduces the level of aluminum to as low as 96 ppb. During the 40 degree centigrade stability testing of that product, the level increased to as much as 380 ppb. This patent teaches the methods necessary to process source plasma (human) through to an albumin preparation with superior shelf life and with demonstrated labeled values which do not change during the dating period.

Aluminum in albumin is a major concern for clinicians who administer albumin in their practice. Koppel et al., J. Toxicol. Clin. Toxicol. 26(5-6):337-56 October, November 1988.

This invention addresses the use of albumin sources which are essentially low hemoglobin containing such as Source Plasma (Human) as described in the Federal Register. However, the method of this invention and the novel invention products can be albumin originating from genetically engineered sources such as rDNA produced sources and other essentially low hemoglobin containing albumin sources. Because the major source of albumin in the world today is plasma, the method of preparing these compositions will be primarily related to plasma or serum. It is not, for example, directed to hemoglobin containing placenta source preparations. Many methods have been known for recovering purified albumin for infusion from materials containing hemoglobin such as placenta utilized as the starting material. See U.S. Pat. No. 4,197,238 which also provides a survey of methods. See also U.S. Pat. No. 4,169,829 also directed to purified albumin prepared from placental or other hemolyzed blood containing hemoglobin. The novelty of this present invention teaches that monomeric albumin (greater than 99%), being 100% pure by cellulose acetate electrophoresis and free from all residual processing chemicals, can be provided using the method taught in this present invention. The preparation contains essentially no material of a molecular weight greater than dimer albumin. A preparation free of polymerized protein, manufactured from an essentially hemoglobin free albumin source such as Source Plasma (Human), and essentially free from aluminum is heretofore unknown. In addition to these attributes is the ability of the product of this invention to remain at labeled values of contaminants throughout its dating period.

An object of this invention is to provide a long shelf life albumin. A further object of this invention is to provide an economical and safe procedure and product, comprising albumin as the major component, useable in medical treatment, from sources essentially free of hemoglobin as a starting material. The ability of this composition to remain essentially free of aluminum permits lasting label levels throughout the dating period of this therapeutic.

The method of manufacture may commence with an albumin source such as the Cohn albumin fractionation scheme at some point relevant to the Fraction V or crude albumin step. The source may also be in-process upstream systems, such as Cohn Fraction IV-1 and Cohn Fraction IV-4. Thin film evaporation techniques may be used to reduce cumbersome volume streams. See Cohn et al. J. Am. Chem. Soc. 68, 459 (1956). The fraction V precipitate or more purified Cohen Fraction state is suspended in water, which may be approximately three volumes more or less of cold, pyrogen free, distilled water. The temperature of the water is below room temperature and may be preferably 8° C. plus or minus 4°. A solution kept at this temperature is formed by thorough mixing. When the precipitate is in solution, the pH is determined and, if necessary, is adjusted so that it should be in the range of 4.5±0.2. The ideal and most preferable pH for this step is 4.5 to 4.6. The pH must always be below 5.0. The albumin is filtered through a depth filter such as is available from AMF Cuno Corp. The filter media must be of such depth that substantially all lipidic proteinaceous material is removed from the starting solution. The albumin filtrate pH is then adjusted to the approximate isoelectric range of α globulins (approximately pH 5.0 to 6.0; preferably, 5.3) with a dilute base solution such as 1.0 Molar sodium carbonate or 1.0 Molar sodium hydroxide. Any convenient base buffering system may be utilized to accomplish the elevation of pH.

Following the pH adjustment, the system at the above described temperature is prepared to undergo a heat shock. First, a quantity of sodium caprylate is added to the system based on the protein concentration of the system during heat shock, i.e., for each kilo of protein available in the filtrate, approximately 30 grams of sodium caprylate is introduced into the system. Ethanol such as SDA-3A alcohol is added to the stabilized albumin filtrate on a per volume basis to equal from approximately 10% to 20% alcohol. During thorough agitation the temperature of the system reaches approximately 20° C. and is thereafter elevated from about 20° C. to approximately 50° C. The preferred temperature elevation is to 50° C. This temperature is maintained for a period of at least one hour, and the preferred range is approximately one to three hours. Generally, the higher the temperature reached the less time at temperature is required. Therefore even though lesser temperature elevations may be employed they will necessitate unduly long dwell time at temperature. When the heat shock is completed, the system temperature may be reduced to normal plasma processing temperatures, such as less than about 10° C. One gram of DEAE Sephadex (Pharmacia Inc.) is added per liter of solution, and the system is filtered through an appropriate depth media such as that supplied by AMF Cuno Corp. The purified albumin filtrate pH is then adjusted from approximately 6.0 to about 8.5 (most preferably 7.2). The purified albumin is then loaded on an ultrafilter such as that built by Romicon, Inc., or the Koch Co. The albumin solution is diafiltered, and the volume replacement is accomplished using a weak salt solution such as 3% sodium chloride or sodium acetate or in some cases sodium caprylate solutions most preferably sodium chloride. The purified albumin solution is diafiltered, and as a result of displacement of the salts, the aluminum and other contaminants are removed. A diafiltration against water (most preferably four volumes of cold distilled water) is performed. The purified, washed albumin is harvested from the ultrafiltration equipment at such a concentration to yield the desired protein level allowing for the addition of excipients. The preferred composition of the final product prepared in the above method would have a molarity of caprylate based on the albumin concentration. That is, a 25% protein preparation would be stabilized generally at from 0.02 Molar to approximately 0.1 Molar, and preferentially, a molarity of 0.04 caprylate. Original preparations of E. J. Cohn were "salt poor". The composition of choice of this present invention would contain approximately 0.1 Molar aminoacetic acid to guarantee tonicity in the event of slight dilutions. This resulting composition will have the greatest shelf life and retention of biological activity. The preparation described in this disclosure, if desired, might be finally compounded with 0.02 Molar sodium caprylate and 0.02 Molar acetyl-dl-tryptophan with sodium chloride to achieve 130 to 160 mEq/L of sodium. The presence of tryptophan in the albumin causes the product to darken with age, and there may be some concern for the products of tryptophan degradation.

EXAMPLE 1

5 Kgs. of Cohn Fraction V paste which had been held in storage for over four years (BR 7209) was processed as lot number 3388-70. The paste was suspended in 3 volumes of +5° C. distilled water and thoroughly mixed for a period of 2 hours. The pH of the solution, read directly on a Beckman pH meter, was 4.65. An AMF Cuno multicartridged filter housing was prepared with two disposable Cuno filter cartridges with the Cuno designation of "90 Sp". The filter system was rinsed with one hundred liters of hot and sixty liters of cold distilled water to remove manufacturing debris from the depth media. The Fraction V solution, with filter aid, was then passed through the filter housing, and a filtrate of less than 10 National Turbidity Units (Hach Nephelometer, Loveland, Co.) was collected. When the filtration was complete, the filter housing was rinsed with +5° C. distilled water in the amount to displace the soluble protein from the filter media. Determinations were made to confirm the recovery of better than 98% of the protein originally suspended. The filtrate pH was 4.66. The pH of the filtrate was adjusted to 5.15 using 1.0 Molar sodium carbonate. Based on the amount of albumin protein present, 30 grams of sodium caprylate per kilo of Fraction V paste were added, followed by the addition of 181 grams of SDA3A alcohol for each liter of albumin filtrate being processed. The temperature of the alcoholic albumin filtrate was then elevated to 50° C. and held at this temperature for 2 hours. The heat shocked material was then chilled to 8° C. One gram of DEAE Sephadex (Pharmacia) was added for each liter of material. A Cuno filter as described above was utilized to remove the denatured globulins and the insoluble DEAE Sephadex (Pharmacia) that had just been added. The filtrate was analyzed for recovered protein and found to contain 97% of the starting available protein. The solution turbidity was less than 10 National Turbidity Units. The ultra pure albumin filtrate pH was adjusted to 7.22, using 1.0 Molar sodium carbonate. The filtrate was then loaded on a pilot model ultrafilter equipped with PM 30 Romicon hollow fiber ultrafilter cartridges (a product of Rohm & Hass). Three volume exchanges were made using 3% simple saline. Permeate flux rates were very good, and rates over 200 mL/cartridge/per minute were common. Five volume exchanges temperatures were always held at less than 10° C. The product was concentrated and harvested from the ultrafilter. The protein concentration was determined to be 26.5%, and the product turbidity was less than 5 National Turbidity Units. There is some concern that the caprylate used during the heat shock would bind to the albumin and an excessive amount of caprylate would create a problem. Neat samples of the product were heated at 60° C. and were found to gel within 10 minutes which demonstrated the reduction of caprylate from the heat shock to a level of no concern. Samples were compounded into a final container configuration as described above, and terminally heat treated for at least ten hours at 60° C. and the table explains the test results.

TABLE I

| Sample # | Formula | Protein | CAE* | HPLC** | Aluminum |
|---|---|---|---|---|---|
| 3388-70A | 0.2M Caprylate/tryptophan | 24.7 | 100% | 0% Vo | <29 ppb |
| 3388-70E | 0.4M Caprylate 0.1M Glycine | 26.5% | 100% | 0% Vo | <29 ppb |

*Cellulose Acetate Electrophoresis
**High Pressure Liquid Chromatography
Turbidity on Hach Co. Nepholometer is 1.4 N.T.U.

BRIEF DESCRIPTION OF THE DRAWINGS

FIG. 1 comprises the albumin level of albumin of this invention compared to commercial albumin in accelerated time study at 40° C. both stored in aluminum containing containers.

FIG. 2 compares the aluminum level of albumin of this invention with aluminum level of commercially available albumin of various manufacturers A through E.

FIG. 3 compares the heavy molecular weight components in the albumin of this invention with the heavy molecular weight components of commercially available albumin of various manufactures A through E, all measured by High Pressure Liquid Chromatography (HPLC).

FIG. 4 compares the purity of the albumin of this invention compared to the purity of commercially available albumin of various manufactures A through E all measured by Cellulose Acetate Electrophoresis (CAE).

FIG. 5 compares the turbidity level of the albumin of this invention with the turbidity level of commercially available albumin of various manufactures A through E all measured in National Turbidity Units (NTU) on a Hach Nephelometer.

What is claimed is:

1. A method of preparing human albumin which is substantially monomeric essentially free of aluminum contaminants and remains so during extended storage, comprising the sequential steps of:

A. adding water to an albumin source to make a first suspension;
B. adjusting the pH of said first suspension to less than 5;
C. removing solids from said first suspension;
D. adjusting the pH to from about 5 to about 6;
E. adding sodium caprylate and ethanol to form a 10 to 20% alcohol second suspension;
F. elevating the temperature of the resulting second suspension to a range of temperatures above said second suspension starting temperature, said range of temperatures being from about 20° C. to about 50° C.;
G. maintaining said second suspension at the elevated temperature for a period of at least about one hour;
H. reducing the second suspension temperature to a range of temperatures less than about 10° C.;
I. removing the solids from the second suspension; and then
J. diafiltering the resultant filtrate while at a pH of from about 6 to about 8.5 with an ionic diafiltration buffer.

2. The method of claim 1 further comprising terminally heat treating for at least ten hours at about 60° C.

* * * * *